United States Patent
Ströfer et al.

(10) Patent No.: US 7,431,804 B2
(45) Date of Patent: *Oct. 7, 2008

(54) METHOD FOR CARRYING OUT THE DISTILLATION OR REACTIVE DISTILLATION OF A MIXTURE CONTAINING AT LEAST ONE TOXIC CONSTITUENT

(75) Inventors: Eckhard Ströfer, Mannheim (DE);
Gerd Kaibel, Lampertheim (DE);
Achim Stammer, Mobile, AL (US);
Carsten Oost, Bad Dürkheim (DE);
Martin Sohn, Mannheim (DE);
Manfred Stroezel, Ilvesheim (DE);
Walter Dobler, Schwetzingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 556 days.

This patent is subject to a terminal disclaimer.

(21) Appl. No.: 10/477,466

(22) PCT Filed: May 17, 2002

(86) PCT No.: PCT/EP02/05517

§ 371 (c)(1),
(2), (4) Date: Nov. 12, 2003

(87) PCT Pub. No.: WO02/094432

PCT Pub. Date: Nov. 28, 2002

(65) Prior Publication Data

US 2004/0150123 A1 Aug. 5, 2004

(30) Foreign Application Priority Data

May 18, 2001 (DE) ................. 101 24 386

(51) Int. Cl.
*B01D 3/28* (2006.01)
*B01D 3/42* (2006.01)
*B01V 19/32* (2006.01)

(52) U.S. Cl. ............................ 203/1; 203/28; 203/89; 203/100; 203/DIG. 6; 261/95; 261/112.1; 261/128; 261/DIG. 72

(58) Field of Classification Search .................... 203/1, 203/28, 29, 89, 100, DIG. 6; 261/95, 128, 261/112.1, 112.2, DIG. 72
See application file for complete search history.

(56) References Cited

U.S. PATENT DOCUMENTS 4,604,247 A * 8/1986 Chen et al. .................... 261/94

(Continued)

FOREIGN PATENT DOCUMENTS

DE 196 05286 8/1997

(Continued)

OTHER PUBLICATIONS

Derwent Abst. DE 10027779, Dec. 2001.
Derwent Abst. EP 54 634, Jun. 1982.

*Primary Examiner*—Virginia Mancharan
(74) *Attorney, Agent, or Firm*—Novak Druce + Quigg LLP

(57) ABSTRACT

A process is proposed for the distillation or reactive distillation of a mixture that includes at least one toxic component, the process being carried out in a column containing a structured packing, having at least one packing layer (1) having a lower end (2) and an upper end (3), the packing layer having an internal geometry varying over its height, in such a manner that in the distillation or reactive distillation, in a first, lower region (6) of the packing layer (1) a bubbling layer having a predominantly disperse gas phase can be established and simultaneously in a second, upper region (7) of the packing layer (1) a film flow having a predominantly continuous gas phase can be established.

6 Claims, 7 Drawing Sheets

U.S. PATENT DOCUMENTS

Figure 1:
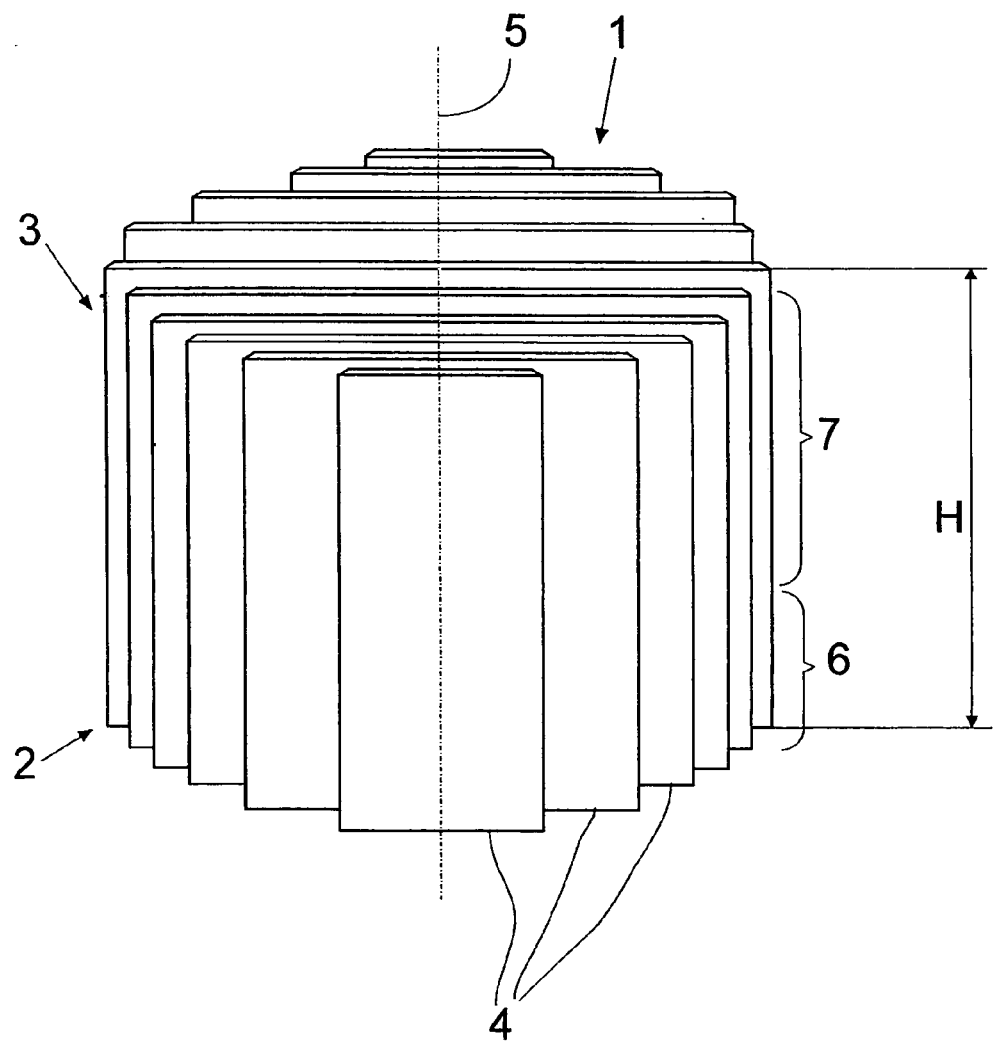

| | | |
|---|---|---|
| 5,360,931 A | 11/1994 | Bohmholdt et al. |
| 5,632,934 A * | 5/1997 | Billingham et al. ...... 261/112.2 |
| 5,762,668 A * | 6/1998 | Lee et al. ...................... 55/486 |
| 5,950,454 A | 9/1999 | Burst et al. |
| 6,423,235 B1 * | 7/2002 | Shimoi et al. ................ 210/760 |
| 6,427,985 B1 | 8/2002 | Kaibel et al. |
| 6,478,290 B1 * | 11/2002 | Ender et al. ............... 261/112.2 |
| 6,713,158 B2 * | 3/2004 | McKeigue et al. .......... 428/184 |
| 7,052,000 B2 * | 5/2006 | Zich et al. ..................... 261/97 |

FOREIGN PATENT DOCUMENTS

| | | |
|---|---|---|
| DE | 199 36380 | 2/2001 |
| DE | 100 2779 | 12/2001 |
| EP | 054 634 | 6/1982 |

* cited by examiner

METHOD FOR CARRYING OUT THE DISTILLATION OR REACTIVE DISTILLATION OF A MIXTURE CONTAINING AT LEAST ONE TOXIC CONSTITUENT

This application is a 371 of PCT/EP02/05517, filed May 17, 2002.

The invention relates to a process for the distillation or reactive distillation of a mixture that comprises at least one toxic component, and to an apparatus for this purpose.

For heat exchange and mass transfer between liquid and gaseous media, in particular for separating mixtures by distillation, plate columns and packed columns are used in industry. The two types differ with respect to the hydrodynamic operating conditions.

In plate columns, in each case a bubbling layer forms on the individual plates where predominantly the liquid is the continuous phase and the gas is the disperse phase. Between the individual plates are free spaces in which predominantly the gas is the continuous phase.

The mode of operation of packed columns differs from plate columns with respect to hydrodynamics. In this case it is not the liquid but the gas which forms the continuous phase. The liquid runs as a film downward over the packings.

Structured packings are made up of a multiplicity of individual layers of packing elements, such as metal sheets, expanded metals and wire fabrics, which are disposed vertically to one another in a regular structure and are usually held together in a composite by attachments such as metal wires, thin metal rods or metal sheet strips. Usually the packing elements themselves have a geometric structuring, for example in the form of folds or circular holes of from about 4 to 6 mm in diameter. The openings act to increase the flood limit of the packing and to make a higher column load possible.

Examples are packings of the types "Mellapak", CY and BX from Sulzer AG, CH-8404 Winterthur, or types A3, BSH or B1 from Montz GmbH, D-40723 Hilden. The folds of the packing elements of these packings run linearly and at an angle of from about 30° to 45° to the longitudinal axis of the packing. The foldings of the packing elements lead to a cross-channel structure within the structured packing.

DE-A 196 05 286 describes a special development in which this angle is further decreased to values of from 3° to 14° in order to reduce the pressure drop of the packings as far as possible in the case of applications at high vacuum (approximately 1 mbar top pressure).

In the prior art, structured packings are known which are catalytically active. A catalytically active distillation packing in a conventional shaping is, for example, the packing "KATAPAK" from Sulzer AG, CH-8404 Winterthur.

Structured packings are usually provided as individual packing layers which are then arranged in the column stacked one above the other. The packing layers generally have a height of from about 0.17 m to about 0.30 m.

In the prior art, a structured packing called "Montz" A2 from Montz GmbH, D-40723 Hilden is known, which has folded packing elements with curved fold courses. Within a packing element, the gradient of these fold courses varies over the height of the packing element. In this case the layers of the packing elements alternate so that in each case one packing element in which the gradient of the fold line is greatest at the bottom end of the packing layer is situated next to a packing element in which the gradient of the fold line is greatest at the top end of the packing layer. The internal geometry of the packing layer is therefore constant over its height. However, this packing type, in comparison with the usual structured packings, has an unfavorable separation efficiency.

Because of the industrial importance of heat exchange and mass transfer processes in chemistry and process engineering, in particular separation by distillation, a multiplicity of technical developments are aimed at improving heat exchange and mass transfer columns, in particular distillation columns. Important criteria for an efficient economic heat exchange and mass transfer column, in particular distillation column, are its price, its throughput performance for the gas and liquid stream and the separation efficiency based on the height of the column. The separation efficiency is usually characterized as the number of theoretical plates per meter of column height ($n_{th}/m$) or as the height equivalent to a theoretical plate (HETP).

German patent application 199 36 380.3 (equivalent to NAE 19980787), which does not have an earlier priority than the present application, discloses a structured packing for heat exchange and mass transfer that ensures improved throughput and economic efficiency of heat exchange and mass transfer columns, in which the structured packing is made up with an internal geometry varying over its height so that, in operation of the packing, in its lower region a bubbling layer having a predominantly disperse gas phase is formed in a targeted manner and simultaneously in its upper region film flow having a predominantly continuous gas phase is formed in a targeted manner.

In chemical engineering, in many applications mixtures that comprise at least one toxic component must be worked up. Examples of particularly critical components are processes for preparing and purifying isocyanates that operate with phosgene as a reaction component, or processes in which prussic acid occurs. For safety reasons attempts are made to keep the amount of toxic substances as low as possible.

It is an object of the present invention, thus to provide a process for the distillation or reactive distillation of a mixture that comprises at least one toxic component, in which process the amount of toxic substances in the column is reduced compared with known processes of the same throughput and the same separation efficiency.

We have found that this object is achieved by means of a process for the distillation or reactive distillation of a mixture that comprises at least one toxic component. The invention features carrying out the process in a column having a structured packing having at least one packing layer with a lower end and an upper end, the packing layer having an internal geometry which varies over its height so that in the distillation or reactive distillation in a first, lower region of the packing layer a bubbling layer having a predominantly disperse gas phase can be established in a targeted manner and simultaneously in a second, upper region of the packing layer film flow having a predominantly continuous gas phase can be established in a targeted manner.

It has surprisingly been found that the amount of toxic substances present in a column can be reduced to a considerable extent, that is to say by a factor of about from 2 to 4, if structured packings are used as are described in German patent application 199 36 380.3, which does not have an earlier priority than the present application. According to the invention the amounts of toxic substances in the column is minimized by using structured packings having an internal geometry varying over the height of the packing layers. By the special shaping, the packing can be operated by targeted measures in a region in which the liquid in the defined subregions forms the continuous phase and in other subregions forms the disperse phase. It is possible, by suitable choice of the amounts of liquid and gas, to operate the packing in such a manner that in the lower region of the packing layer a bubbling layer having a disperse gas phase forms in a targeted manner and, in the upper region of the packing layer a film flow of the liquid having a continuous gas phase forms in a targeted manner.

It is known that in packings flooding occurs when the liquid streams and gas streams exceed certain values. A feature of the transition to the flooding state with increasing loading is that the liquid which is initially flowing out in disperse form as a film is converted into a new operating state in which the liquid is the continuous phase, similar to a bubble column. A feature of this state is marked pressure increase and drastic decrease in separation efficiency, since the liquid is back-mixed over a large height region. The inventively used packing limits this flooded state to a lower subregion. In a further upper subregion, in contrast, the packing is operated as usual, so that the liquid flows out as a film on the packing surface. This subregion further acts as demister.

These hydrodynamic operating stages described can be achieved, in particular, by the packing layer being formed having a varying resistance to flow over its height, the lower region of the packing layer having a greater resistance to flow than the upper region of the packing layer. The lower region and the upper region preferably extend in each case over the entire cross-sectional area of the packing layer.

Preferably, a structured packing is used in which the packing layer has touching flat packing elements, in particular folded metal sheets, expanded metals, wire fabrics and knitted meshes, the fold line varying over the height of the packing layer in such a manner that, in the lower region of the packing layer, it is at a greater angle to the longitudinal axis of the packing layer than in the upper region of the packing layer.

However, it is also possible to form packing elements having a fold line which has a curved course, in particular in such a manner that the angle between the tangent to the fold line and the longitudinal axis of the packing layer decreases from about 45 to 75°, preferably from 60 to 70°, in the lower region of the packing layer, to from 10 to 45°, preferably from 30 to 45°, in the upper region of the packing layer. This curved fold line course is particularly easy and thus economic to fabricate.

However, it is also possible to provide other courses of the folds, for example two or more courses which are linear in sections.

It has surprisingly been found that a further improvement of the separation efficiency of the packing is possible by constructing the individual packing layer, as a departure from the previously industrially conventional height of from about 0.18 to 0.30 m, with a smaller height, in particular of from about 0.10 to 0.15 m. In this case lower values from the abovementioned range, in particular for closely packed packings, that is to say packings having a specific surface area of from about 500 to 750 m$^2$/m$^3$ are particularly suitable, and in contrast higher values of the packing height are particularly suitable for coarser packings having a specific surface area of from about 100 to 500 M$^2$/m$^3$.

In a preferred embodiment of the present invention in which the packing layer has packing elements, at least some of the packing elements are bent over in a tongue-like manner at the lower end and/or at the upper end of the packing layer. Preferably, the packing elements have cuts for this at the lower end and/or at the upper end of the packing layer at defined distances which preferably correspond to about half the fold width, so that tongues can be bend over in different directions. Particularly preferably, the tongues are bent over alternately toward both sides of the packing element. The depth of the cuts is preferably from 3 to 8 mm.

The angle which the bent-over tongues make with the packing element is preferably from about 110 to 150°, so that the tongues are roughly horizontally oriented in the packing layer. The lateral extension of the tongues is chosen so that from about 30 to 60% of the flow cross section is blocked. Preferably, only every second sequential packing element is bent over laterally in order to ensure sufficient mechanical stability of the packing layers stacked one above the other.

In a further preferred embodiment, the packing layer is composed of a combination of at least one first partial packing layer and one second partial packing layer, the first and second partial packing layers differing from one another with respect to their internal geometries.

The first packing layer is disposed underneath the second packing layer. Particularly preferably, the first packing layer and the second packing layer are disposed directly one over the other, the first packing layer forming the lower partial packing layer and the second packing layer forming the upper partial packing layer. The partial packing layers are preferably designed so that their internal geometry does not vary over their height. The first lower partial packing layer preferably has a height of from 0.02 to 0.10 m, and particularly preferably from 0.03 to 0.05 m. The second upper partial packing layer preferably has a height of from 0.05 to 0.2 m, particularly preferably from 0.10 to 0.15 m. The resistance to flow of the first partial packing layer per meter of height is preferably from about 1.2 to about 5 times, particularly preferably from about 1.5 to about 2.5 times, as high as the resistance to flow of the second partial packing layer. If the partial packing layers are composed of packing elements having folds, the resistance to flow of the partial packing layers can be set by the angle which the fold courses or tangents of the fold courses make with the longitudinal axis of the packing layers. The larger this angle, the higher the resistance to flow. In the context of the present invention, an embodiment is preferred in which the partial packing layers are composed of packing elements having folds, the fold courses or tangents of the fold courses of the first partial packing layer being at a greater angle to the longitudinal axis of the packing layer than the fold courses or tangents of the fold courses of the second partial packing layer. Preferred angles have already been mentioned above, which are here incorporated by reference. The resistance to flow of the partial packing layers can, furthermore, also be achieved by the size of the specific surface area per unit volume.

Preferably, the partial packing layers have different specific surface areas per unit volume. Particularly preferably, the first lower partial packing layer has a higher specific surface area per unit volume than the second upper partial packing layer. In this case the specific area of the first lower partial packing layer is preferably from 20 to 100%, particularly preferably from 30 to 60%, greater than that of the second upper packing layer.

The invention also relates to a column for carrying out the inventive process. The column containing structured packings, as are described in the German patent application which does not have a priority earlier than the present application, is used inventively in an embodiment in which the liquid collector and distributor is dispensed with. It has surprisingly been found that the abovementioned structured packings have the advantageous property that they have a certain distribution action which is completely sufficient for connection purposes of redistribution of liquid. As a result the liquid holdup in the column and the total volume of the column can be further reduced. Only at the top of the column and at the feed point are distribution apparatuses of a simple type, such as ring distributors, provided for the liquid. Preferably, at least in the lower region of the packing layer perforated packing materials are used, preferably having a perforation content of from 5 to 50%, particularly preferably from 10 to 20%, in order to improve the cross distribution of the liquid in the flooded region.

In a further preferred embodiment of an inventive column, the amount of toxic substances in the column can be further reduced by integrating the condenser at the column top into the column. As a result the liquid holdup is further reduced. In this measure, recourse can be made to designs which are customary in distillation technology and have been proved in practice.

Figure 2:
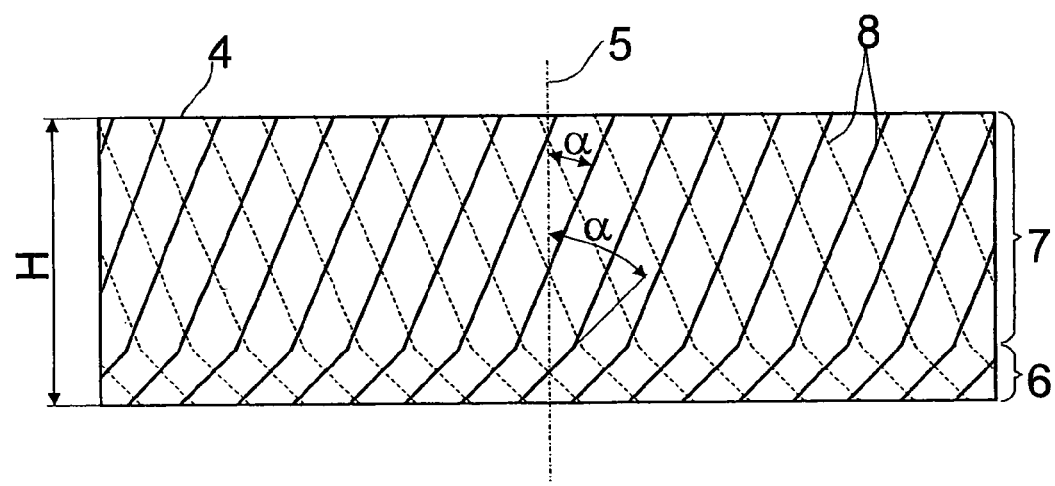
Figure 3:
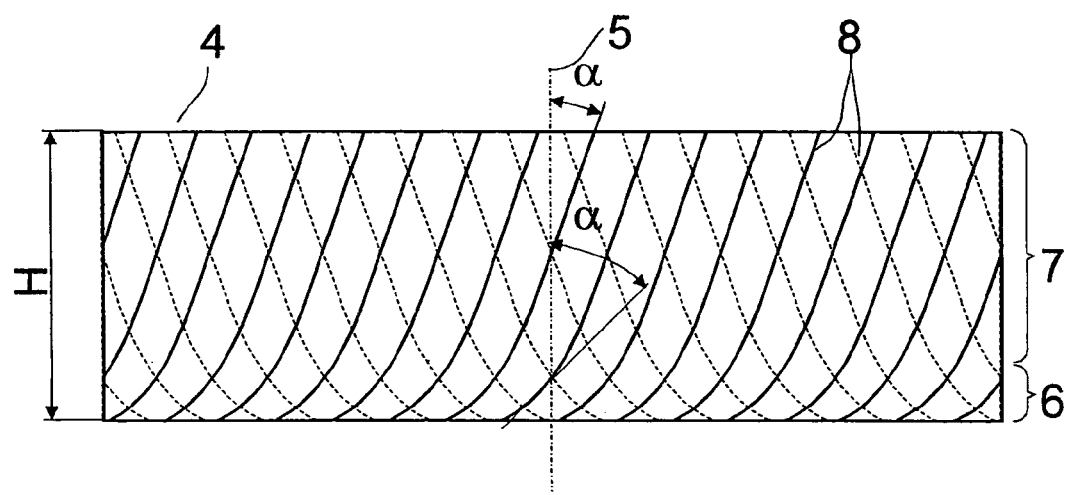
Figure 4:
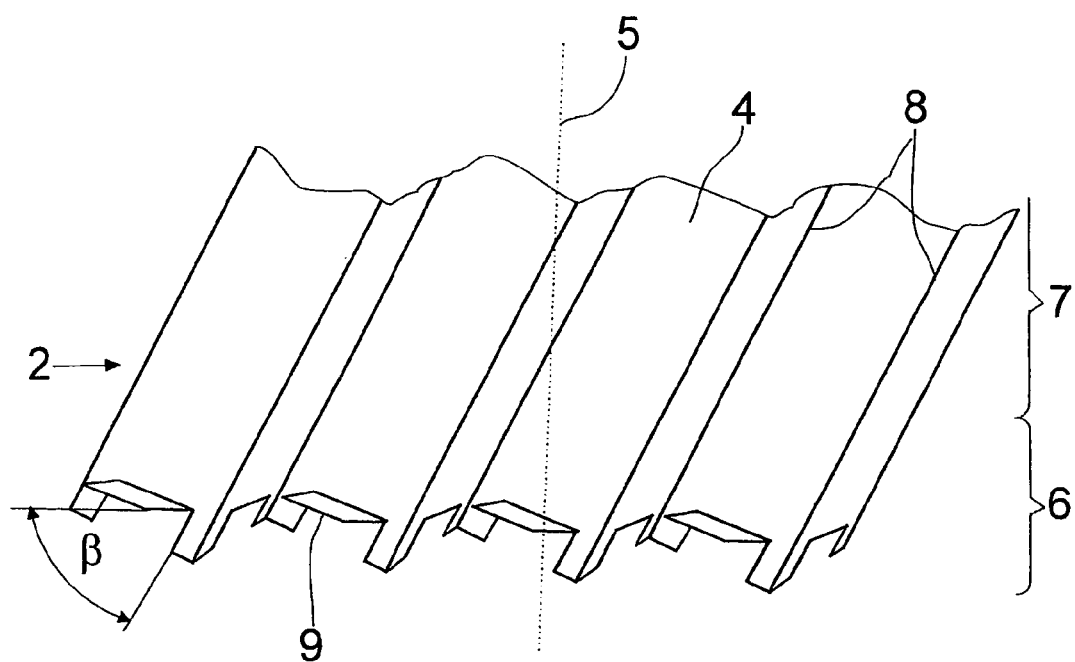
Figure 5:
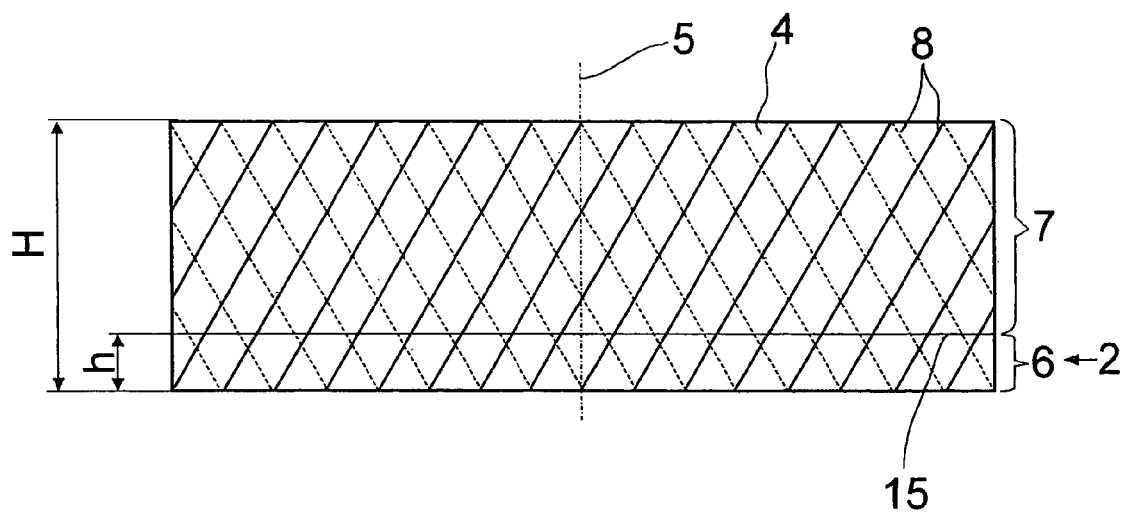
Figure 6:
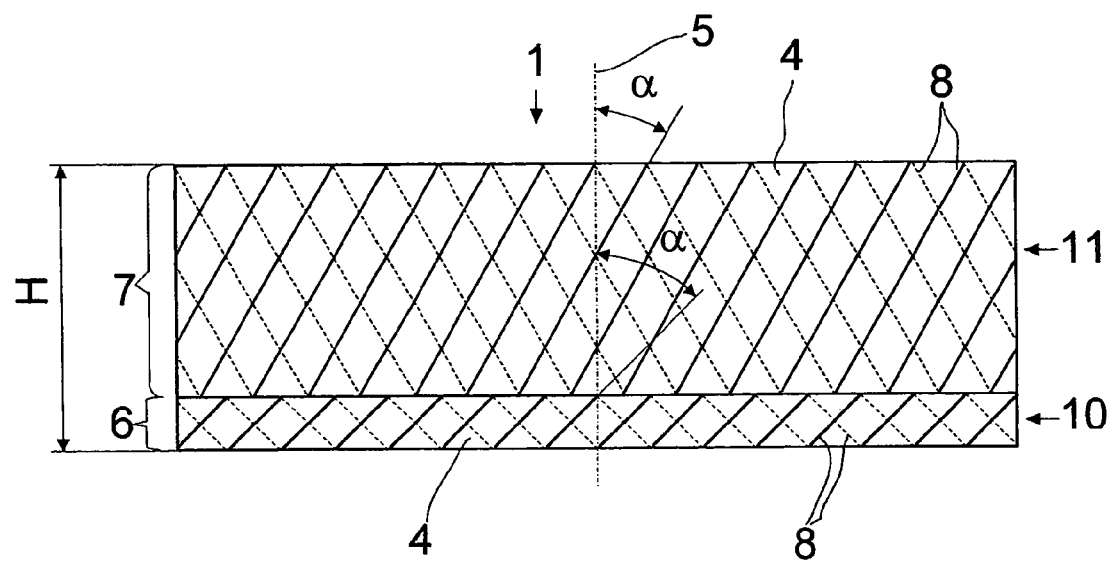
Figure 7:
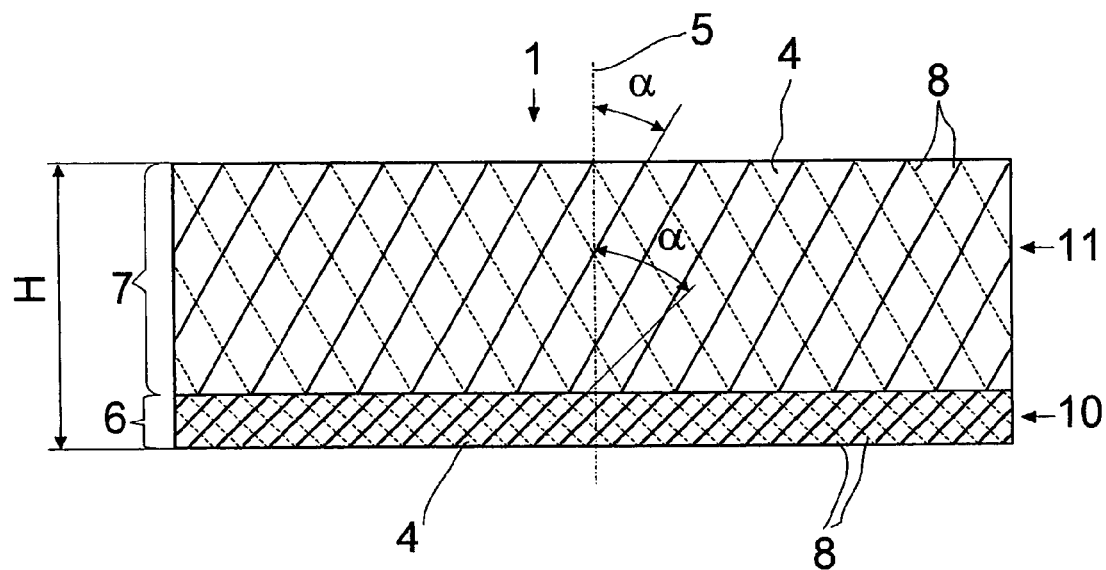

The invention is described in more detail below with reference to examples and a drawing. In the drawing:

FIG. 1 shows a packing layer 1 of an embodiment of the structured packing,

FIG. 2 shows serially arranged packing elements 4 of a packing layer 1 of an embodiment of the structured packing, FIG. 3 shows serially arranged packing elements 4 of a packing layer 1 of a further embodiment of a structured packing, FIG. 4 shows a section of a packing element 4 of a packing layer 1 of an embodiment of a structured packing having laterally bent-over packing elements 4, in a three-dimensional view, FIG. 5 shows serially arranged packing elements 4 of a packing layer 1 of a further embodiment of the structured packing having thin strips 15 between the packing elements 4, FIG. 6 shows a further embodiment of the structured packing having a packing layer 1 that is formed from two partial packing layers of different internal geometry and FIG. 7 shows a further embodiment of the structured packing having a packing layer 1 that is formed from two partial packing layers of different internal geometry.

In the figures, the same reference numbers denote the same or equivalent features.

FIG. 1 shows a packing layer 1 of an embodiment of a structured packing according to the present invention. The packing layer 1 has a first, lower end 2 and a second, upper end 3. It has a height H of, for example, 0.2 m. The packing layer has mutually contacting flat packing elements 4 made of metal sheets provided with folds (not shown). The reference number 5 shows the longitudinal axis of the packing layer 1. The packing layer 1, in addition, has a circular cross section. The internal geometry of the packing layer 1 varies over its height (not shown). The packing layer 1 has a first, lower region 6, whose internal geometry differs from a second, upper region 7. The first, lower region 6 of the packing layer 1 has a greater resistance to flow than the second, upper region 7. By suitable setting of the liquid and gas flow rates, a bubbling layer with a predominantly disperse gas phase forms in the first, lower region 6 of the packing layer 1 and simultaneously a film flow of the liquid with a predominantly continuous gas phase forms in the second, upper region 7 of the packing layer. The first, lower region 6 of the packing layer 1 and the second, upper region 7 of the packing layer 1 extend over the entire cross-sectional area of the packing layer 1. In addition, the first, lower region 6 is directly joined to the second, upper region 7. The second, upper region 7 of the packing layer 1 bounds the second, upper end 3 of the packing layer 1 and the first, lower region 6 bounds the first, lower end 2 of the packing layer 1.

FIGS. 2 and 3 each show diagrammatically serially arranged packing elements 4 of a packing layer 1 of different embodiments of the structured packing according to the present invention. The continuous lines show the fold courses of the first, third, fifth etc. packing element 4 and the dashed lines show the fold courses of the second, fourth, sixth etc. packing element 4.

The packing elements 4 in FIG. 2 have the same height H of, for example, 0.2 m, as the packing layer 1. The packing elements 4 consist of metal sheets with folds 8, as a result of which the packing layer 1, which is made up of these packing elements, receives a cross-channel structure. The folds 8 have a linear course in sections. In the first, lower region 6 of the packing layer 1 the fold courses are at a larger angle α to the longitudinal axis 5 of the packing layer 1 than in the second, upper region 7 of the packing layer 1. In the first, lower region 6 of the packing layer 1 the fold courses are at an angle α of about 60° to the longitudinal axis 5 of the packing layer 1. In the second, upper region 7, the fold courses are at an angle α of about 30° to the longitudinal axis 5 of the packing layer 1.

FIG. 3 shows diagrammatically packing elements 4 of a packing layer 1 of a further embodiment of the structured packing. The packing elements 4 have folds 8 with continuously curved fold courses. The packing elements 4 have the same height H, of for example 0.2 m, as the packing layer 1. The tangents to the fold courses are, in the first, lower region 6 of the packing layer 1 at a larger angle α to the longitudinal axis 5 of the packing layer 1 than in the second, upper region 7 of the packing layer 1. In the first, lower region 6 of the packing layer 1 the tangents to the fold courses are at an angle of from about 45° to about 75° to the longitudinal axis 5 of the packing layer 1. In the second, upper region 7, the tangents to the fold courses are at an angle α of from about 10° to about 45° to the longitudinal axis 5 of the packing layer. The folds 8 have an approximately parabolic course.

FIG. 4 shows, in three-dimensional view, a detail of a packing element 4 of a further embodiment of the inventive packing. The packing element 4, in the detail shown, has folds 8 with a linear course. The reference number 5 denotes the longitudinal axis of the packing layer 1 in which the packing element 4 shown is disposed. At the first, lower end 2 of the packing layer 1, at distances which correspond to roughly half the fold width, cuts which are from about 3 to 8 mm wide are introduced into the packing element 4 and tongues 9 are alternately bent over toward both sides so that they are at an angle β of from 110° to 150° to the packing element, so that the tongues are roughly horizontally oriented in the packing layer. The lateral extension of the tongues is chosen so that from about 30 to 60% of the flow cross section is blocked.

FIG. 5 shows serially arranged packing elements 4 of a packing layer 1 in a further embodiment of the structured packing. The continuous lines show the fold courses of the first, third, fifth etc. packing element 4 and the dashed lines show the fold courses of the second, fourth, etc. packing element 4. The packing elements 4 have the same height H, of for example 0.2 m, as the packing layer 1. The packing elements 4 have linear folds 8. The reference number 5 designates the longitudinal axis of the packing layer 1. At the first, lower end 2 of the packing layer 1, thin metal sheet strips 15 are disposed between the packing elements 4. The metal sheet strips are joined directly to the lower end 2 of the packing layer 1. The strips are planar and preferably have a height h of from about 15 to 25 mm.

FIG. 6 shows in longitudinal section a packing layer 1 of an embodiment of the inventive structured packing. The packing layer 1 consists of two partial packing layers arranged one above the other, a first partial packing layer 10 and a second partial packing layer 11. Both partial packing layers 10, 11 together form the height H of the packing layer 1. The first partial packing layer 10 forms the lower partial packing layer and the second partial packing layer 11 forms the upper partial packing layer. The first partial packing layer 10 forms the first, lower region 6 of the packing layer 1, and the second partial packing layer 11 forms the second, upper region 7 of the packing layer 1. Both partial packing layers consist of a plurality of packing elements 4 which are arranged next to one another or serially. The packing elements 4 of the partial packing layers 10, 11 consist of metal sheet and have folds 8 which run linearly. The continuous lines show the fold courses of the first, third, fifth etc. packing element 4 and the dashed lines show the fold courses of the second, fourth, sixth etc. packing element 4. The fold courses are at an angle α to the longitudinal axis 5 of the packing layer 1, in the first partial packing layer 10, which is larger than the angle which the fold courses in the second partial packing layer 11 are at to the longitudinal axis 5. In the first partial packing layer 10, the fold courses are at an angle α of about 60° to the longitudinal axis of the packing layer 1. In the second partial packing layer 11 the fold courses are at an angle α of about 30° to the longitudinal axis of the packing layer 1. The first partial packing layer 10 as a result has a greater resistance to flow than the second partial packing layer 11. The first partial packing layer 10 preferably has a height of from 0.02 to 0.10 m, particularly preferably from 0.03 to 0.05 m.

FIG. 7 shows, as does FIG. 6, an embodiment of the inventive structured packing in longitudinal section, with a packing layer 1 which consists of two partial packing layers 10, 11. The two embodiments of FIGS. 6 and 7 essentially agree. The same reference numbers designate the same parts. Reference is thus made to the comments on FIG. 6. In contrast to the embodiment in FIG. 6, the fold courses of the present embodiment of FIG. 7 are at the same angle α to the longitudinal axis 5 of the packing layer 1 in the first and second partial packing layers 10, 11. However, the lower partial packing layer 10 has a specific surface area which is greater by 50% than that of the upper partial packing layer 11. As a result, the resistance to flow is greater in the first, lower partial packing layer 10 than in the second, upper partial packing layer 11.

By suitably setting the liquid and gas flow rates, in all of the embodiments of the inventive structured packing described in FIGS. 1 to 7, a bubbling layer having a predominantly disperse gas phase forms in a targeted manner in the first, lower region 6 of the packing layer 1 and, simultaneously, a film flow of the liquid having a predominantly continuous gas phase forms in a targeted manner in the second, upper region 7 of the packing layer 1.

EXAMPLE

The experimental column used was a metal column made of stainless steel having an internal diameter of 0.1 m and a total height of 6.2 m. It was packed with structured sheet metal packings in cross-channel structure, the column packings having alternately different specific surface areas. The packings were each composed of a 0.035 m high packing layer having a specific surface area of 500 m²/m³ (type Montz B1-500) and a 0.195 m high packing layer disposed above it having a specific surface area of 250 m²/³ (type Montz B1-250). The folds were at an angle to the longitudinal axis of the column, for both types of packing, in each case of 45° against the horizontal. Both the low packings and the high packings were equipped on their periphery with liquid scrapers made of wire mesh in order to avoid the liquid being able to pass via the rim. The low sheet metal packings had circular perforations of diameter 4 mm. In the enrichment part of the column, a total of 0.92 m of packings were installed. The stripping part of the column had a packing height of 2.07 m.

A trapping tray was mounted at the feed point of the column. The influent liquid was applied to the trapping tray and passed from there to an attached natural circulation evaporator which served as a reboiler. The gas/liquid mixture exiting from this evaporator was passed to a second trapping tray below the trapping tray. The liquid on this tray was likewise passed to the evaporator. Excess liquid flowed off via an inserted overflow pipe. At the bottom of the column a natural circulation evaporator was mounted for heating. The vapor was cooled and partially condensed at the top of the column via two sequential condensers which were impinged with cooling water (+22° C.) or brine (−15° C.).

The feed mixture essentially consisted of the components toluene diisocyanate (TDI) (6.4%), hydrogen chloride (1.1%), phosgene (13.6%), monochlorobenzene (66.4%) and higher-boiling byproducts (12.5%) and were fed into the column in a liquid state at a flow rate of 374 kg/h at a temperature of about 101° C. The column was operated at a pressure of 2.65 bar (column top). The heating power of the column bottom was set so as to give a temperature of 166° C. at the bottom of the column. The heating power of the reboiler in the region of the feed point was controlled so that the temperature in the topmost packing layer of the stripping section was 94° C. There was no reflux at the column top. Instead, as reflux liquid, monochlorobenzene was fed in at a feed temperature of 32° C. at a flow rate of 51.6 kg/h. The overhead product obtained in the first condenser was a stream of 30.2 kg/h having a content of about 0.9% hydrogen chloride, 41.5% phosgene and 54.8% monochlorobenzene. In the secondary condenser a stream of about 61 kg/h having a content of about 22.4% of hydrogen chloride, 75.6% of phosgene and 1.2% of monochlorobenzene was produced. The bottom product at a flow rate of 334.3 kg/h was highly depleted in hydrogen chloride and phosgene and only had residual contents of less than 50 ppm of hydrogen chloride and less than 10 ppm of phosgene.

The column was operated in the stripping section with a gas loading factor F of 1.7 $(Pas)^{0.5}$. The packings used in the experimental plant are upscaleable and may be used in a production plant in the same design and loading. As a safety factor, the packing height will be increased in a large scale plant from 2.07 to 3 m. In contrast, in comparable production plants currently 15 valve trays must be used in the stripping section, which occupy a height of 6 m at a tray spacing of 0.4 m. The trays are operated at an F factor of about 0.9 $(Pas)^{0.5}$. The volumetric ratio of packings to trays is thus 3/1.7:6/0.9=0.265. Thus, in the gas space of the column internals with packings, that is to say in the inventive process, only about 26.5% of the toxic substances are present which are present in the case of trays. If the liquid holdup of the packings of about 5% and of the plates of about 3% is taken into account, this gives, as a further advantage with packings, a reduction in liquid holdup of about 44%, compared with a plate column.

We claim:

1. A method for distillation or reactive distillation of a mixture containing at least one toxic component, said method comprising
(A) feeding said mixture in liquid form into a column containing a structured packing having at least one packing layer,
wherein said at least one packing layer has an internal geometry varying over its height, and
wherein said at least one packing layer has a lower region and an upper region, and
(B) operating the column in such a manner that in the lower region of said at least one packing layer a bubbling layer having a predominantly disperse gas phase is established while simultaneously in the upper region of said at least one packing layer a film flow of the liquid having a predominantly continuous gas phase is established in a targeted manner, and wherein said at least one packing layer has a resistance to flow which varies over its height, the lower region of said at least one packing layer having a greater resistance to flow than the upper region of said at least one packing layer, and said at least one packing layer has mutually contacting flat packing elements, said flat packing elements comprising at least one of folded metal sheets, expanded metals, wire fabrics or knitted meshes, wherein a fold line is varied over the height of said at least one packing layer such that said fold line has a greater angle relative to the longitudinal axis of said at least one packing layer in the lower region of said at least one packing layer than in the upper region of said at least one packing layer, and wherein the fold line has a curved course such that an angle between tangents to the fold line and the longitudinal axis of said at least one packing layer decreases from about 45 to 75° in the lower region of said at least one packing layer and to 10 to 45° in the upper region of said at least one packing layer.

2. A method for distillation or reactive distillation of a mixture containing at least one toxic component, said method comprising
(A) feeding said mixture in liquid form into a column containing a structured packing having at least one packing layer,
wherein said at least one packing layer has an internal geometry varying over its height, and
wherein said at least one packing layer has a lower region and an upper region, and
(B) operating the column in such a manner that in the lower region of said at least one packing layer a bubbling layer having a predominantly disperse gas phase is established while simultaneously in the upper region of said at least one packing layer a film flow of the liquid having a predominantly continuous gas phase is established in a targeted manner, and wherein said at least one packing layer has a resistance to flow which varies over its height, the lower region of said at least one packing layer having a greater resistance to flow than the upper region of said at least one packing layer, and wherein said at least one packing layer has mutually contacting flat packing elements, said flat packing elements comprising at least one of folded metal sheets, expanded metals, wire fabrics or knitted meshes, wherein a fold line is varied over the height of said at least one packing layer such that said fold line has a greater angle relative to the longitudinal axis of said at least one packing layer in the lower region of said at least one packing layer than in the upper region of said at least one packing layer, and wherein the fold line has a course which is linear in sections, the fold line in the lower region of said at least one packing layer being at an angle of from 45 to 75° relative to the longitudinal axis of said at least one packing layer, and the angle of the fold line relative to the longitudinal axis of said at least one packing layer decreases toward the top in one or more steps to from 10 to 45°.

3. A method for distillation or reactive distillation of a mixture containing at least one toxic component, said method comprising
(A) feeding said mixture in liquid form into a column containing a structured packing having at least one packing layer,
wherein said at least one packing layer has an internal geometry varying over its height, and
wherein said at least one packing layer has a lower region and an upper region, and
(B) operating the column in such a manner that in the lower region of said at least one packing layer a bubbling layer having a predominantly disperse gas phase is established while simultaneously in the upper region of said at least one packing layer a film flow of the liquid having a predominantly continuous gas phase is established in a targeted manner and, wherein the height of said at least one packing layer is from 0.05 to 0.20 m, and the height of the lower region of said at least one packing layer is from 0.02 to 0.1 m.

4. A method for distillation or reactive distillation of a mixture containing at least one toxic component, said method comprising:
(A) feeding said mixture in liquid form into a column containing a structured packing having at least one packing layer,
wherein said at least one packing layer has an internal geometry varying over its height, and
wherein said at least one packing layer has a lower region and an upper region, and
(B) operating the column in such a manner that in the lower region of said at least one packing layer a bubbling layer having a predominantly disperse gas phase is established while simultaneously in the upper region of said at least one packing layer a film flow of the liquid having a predominantly continuous gas phase is established in a targeted manner, and wherein said at least one packing layer has a resistance to flow which varies over its height, the lower region of said at least one packing layer having a greater resistance to flow than the upper region of said at least one packing layer, and wherein said at least one packing layer has mutually contacting flat packing elements, said flat packing elements comprising at least one of folded metal sheets, expanded metals, wire fabrics or knitted meshes, wherein a fold line is varied over the height of said at least one packing layer such that said fold line has a greater angle relative to the longitudinal axis of said at least one packing layer in the lower region of said at least one packing layer than in the upper region of said at least one packing layer, and wherein the fold line has a curved course such that the angle between tangents to the fold line and the longitudinal axis of said at least one packing layer decreases from 60 to 70° in the lower region of said at least one packing layer and from 30 to 45° in the upper region of said at least one packing layer.

5. A method for distillation or reactive distillation of a mixture containing at least one toxic component, said method comprising
(A) feeding said mixture in liquid form into a column containing a structured packing having at least one packing layer,
wherein said at least one packing layer has an internal geometry varying over its height, and
wherein said at least one packing layer has a lower region and an upper region, and
(B) operating the column in such a manner that in the lower region of said at least one packing layer a bubbling layer having a predominantly disperse gas phase is established while simultaneously in the upper region of said at least one packing layer a film flow of the liquid having a predominantly continuous gas phase is established in a targeted manner, and wherein said at least one packing layer has a resistance to flow which varies over its height, the lower region of said at least one packing layer having a greater resistance to flow than the upper region of said at least one packing layer, and wherein said at least one packing layer has mutually contacting flat packing elements, said flat packing elements comprising at least one of folded metal sheets, expanded metals, wire fabrics or knitted meshes, wherein a fold line is varied over the height of said at least one packing layer such that said fold line has a greater angle relative to the longitudinal axis of said at least one packing layer in the lower region of said at least one packing layer than in the upper region of said at least one packing layer, and wherein the fold line has a course which is linear in sections, the fold line in the lower region of said at least one packing layer being at an angle of from 60 to 70° and the angle of the fold line to the longitudinal axis of said at least one packing layer decreases toward the top in one or more steps from 30 to 45°.

6. A method for distillation or reactive distillation of a mixture containing at least one toxic component, said method comprising (A) feeding said mixture in liquid form into a column containing a structured packing having at least one packing layer, wherein said at least one packing layer has an internal geometry varying over its height, and wherein said at least one packing layer has a lower region and an upper region, and (B) operating the column in such a manner that in the lower region of said at least one packing layer a bubbling layer having a predominantly disperse gas phase is established while simultaneously in the upper region of said at least one packing layer a film flow of the liquid having a predominantly continuous gas phase is established in a targeted manner, and wherein the height of said at least one packing layer is from 0.10 to 0.15 m and the height of the lower region of said at least one packing layer is from 0.03 to 0.05 m.

* * * * *